United States Patent [19]

Hodosh

[11] Patent Number: 5,153,006
[45] Date of Patent: Oct. 6, 1992

[54] METHOD OF TREATING POST-RESTORATION DENTAL PAIN

[76] Inventor: Milton Hodosh, 243 Elmwood Ave., Providence, R.I. 02907

[21] Appl. No.: 743,680

[22] Filed: Aug. 12, 1991

[51] Int. Cl.⁵ .................. A61K 6/00; A61K 6/02; A61K 9/06; A61K 33/00

[52] U.S. Cl. ................. 424/718; 424/49; 106/35; 433/212.1; 433/215; 433/217.1; 433/222.1; 433/224; 433/228.1; 523/115

[58] Field of Search ............. 424/49-58, 424/718; 106/35; 433/217.1, 222.1, 224, 228.1, 212.1, 215

[56] References Cited

U.S. PATENT DOCUMENTS

| | | | |
|---|---|---|---|
| 3,343,608 | 10/1982 | Hodosh | 433/224 |
| 3,863,006 | 1/1975 | Hodosh | 424/49 |
| 4,012,839 | 3/1977 | Hill | 514/495 |
| 4,057,621 | 11/1977 | Pashley et al. | 424/49 |
| 4,283,385 | 8/1981 | Dhabhar et al. | 424/52 |
| 4,357,318 | 11/1982 | Shah et al. | 424/49 |
| 4,400,373 | 8/1983 | Hodosh | 424/49 |
| 4,407,675 | 10/1983 | Hodosh | 523/115 |
| 4,631,185 | 12/1986 | Kim | 424/49 |
| 4,645,662 | 2/1987 | Nakashima et al. | 424/52 |
| 4,751,072 | 6/1988 | Kim | 424/49 |
| 4,992,258 | 2/1991 | Mason | 424/49 |
| 5,015,466 | 5/1991 | Parran et al. | 424/52 |

*Primary Examiner*—Shep K. Rose
*Attorney, Agent, or Firm*—Salter, Michaelson & Benson

[57] ABSTRACT

A method for treating and reducing post-restoration dental pain comprising the application of an agent, the essential ingredient of which is potassium nitrate, to the affected tooth and the cemento-enamel junction thereof.

1 Claim, No Drawings

METHOD OF TREATING POST-RESTORATION DENTAL PAIN

BACKGROUND AND SUMMARY OF THE INVENTION

The present invention deals with the problem of post-restoration dental pain.

It is well known in the field of dentistry that a relatively high degree of pain is encountered by the patient following the placement of dental restorations, which include the penetration of bacteria into dentinal tubules, the caries process with resultant demineralization of tooth matter, caries removal, and tooth preparation resulting from use of a dental drill, the insertion of amalgams, composites, composite restorations/sealants, as well as crown and bridge preparation, impressions, insertion and cementation. All of these types of dental restorations contribute to a lingering post-restoration pain that may remain with the patient for varying periods of time, and that take place even though the teeth of the patient were asymptomatic prior to the rendered dentistry. Post-restoration pain also exists when dissimilar metals, such as gold and silver, contact each other. These dissimilar filling metals can be in different areas in the patient's mouth or may be next to each other in the same arch, but in either case, contact of these dissimilar metals when one of them is newly placed in the patient's mouth results in the emission of electric current in the salty saliva. This condition is known as galvanic shock and is considered to be a type of post-restoration pain with which the instant invention is concerned.

The present invention concerns a treatment that substantially reduces or entirely eliminates the aforesaid post-restoration dental pain, the treatment comprising the application of an agent, the essential ingredient of which is potassium nitrate, to the restoration and the cemento-enamel junction of the teeth involved.

It is important to understand that post-restoration pain is entirely different from the type of pain caused by dentinal hypersensitivity. The pain of dentinal hypersensitivity is not elicited unless tactile, chemical, or thermal stimuli are applied to the tooth, and it (the pain) leaves immediately when the stimulus or irritant of touch, hot, cold, sweet, sour, acid, electrical, etc., is removed. Expressed differently, as soon as the cause of hypersensitivity pain is removed, the pain itself disappears. Hypersensitivity pain does not result from drilling of the teeth, or caries removal procedures, treatment of the teeth by acid etching, etc., but rather this type of pain involves teeth which are intact, and is associated with gingival recession, clenching or bruxing, periodontal disease, and other unknown causes. Although post-restoration pain can be exacerbated by stimuli such as hot or cold, chemical or tactile factors, etc., the post-restoration pain lingers on after the irritant or stimuli is removed. It should also be noted that post-restoration pain can lead to reactive pulpal degeneration, such as abscess, granulonia, cyst, or a combination thereof.

Thus, although applicant has heretofore discovered that potassium nitrate is highly effective for desensitizing hypersensitive teeth (U.S. Pat. No. 3,863,006); and is also highly effective for the treatment of canker sores (U.S. Pat. No. 4,191,750); for preserving dental pulp (U.S. Pat. Nos. 4,343,608 and 4,407,675); and for the treatment of gingival and periodontal tissues (U.S. Pat. No. 4,400,373), it will readily be apparent that all of these other inventions of applicant involve problems entirely different from the problem of post-restoration pain.

DESCRIPTION OF THE INVENTION

It has now been found that post-restoration pain can be greatly reduced or entirely eliminated by applying to the restoration and the cemento-enamel junction of the tooth or teeth involved an agent, the essential ingredient of which is potassium nitrate. The agent may be in the form of a liquid, although for greater efficacy the agent preferably comprises a viscous compound, such as a gel, ointment, paste, or cream. When applied to the restoration and the tooth cemento-enamel junction, the agent penetrates and fills the dentinal tubules somewhat influencing the hollow odontoblastic fibers (tomes fibers) and the odontoblasts. It is assumed that the potassium nitrate affects the fluid dynamics passing into the dentinal tubules influencing the pulp to alleviate or eliminate the post-restoration pain, thus not only eliminating the discomfort to the patient, but also preventing the pulpal degeneration which sometimes results from post-restoration pain.

As previously stated, the agent comprising potassium nitrate is preferably in a viscous form, such as a liquid gel, ointment, paste or cream, so that when applied liberally to the restoration and the cemento-enamel tooth junction, the agent tends to remain in place and is not washed away quickly, thus providing extended intimate contact between the agent and the newly placed restoration and the affected tooth. It has been found that a compound comprising between $\frac{1}{2}\%$ by weight to saturation is effective in achieving the objectives of this invention, although the optimum concentration has been found to be between 4% and 8% by weight of potassium nitrate, it being noted that potassium nitrate is soluble in water and glycerine, whereupon one or both of the latter will normally form a part of the compound formulation. It should be emphasized, however, that other potassium and nitrate preparations have been tried for the purposes of this invention but do not have efficacy in reducing or eliminating painful teeth post-restoration, whereas it has been specifically found that potassium nitrate does achieve the desired objective.

An example of an aqueous potassium nitrate gel which has been effectively used to reduce or eliminate post-restoration pain is as follows:

30 grams - potassium nitrate ($KNO_3$)
17 grams - hydroxyethylcellulose
28 ounces water In the above example, the agent hydrolyses in several hours to form a gel which is easy to apply, flows well, and stays in the area in which it is placed for at least five minutes. The gel can be applied by the dentist in his professional office, or it can be given to the patient to be applied. It is safe and not at all harmful to the oral soft tissues (tongue, palate, and other mucosae).

As this invention may be embodied in several forms without departing from the spirit or essential characteristics thereof, the present embodiment is therefore illustrative and not restrictive, since the scope of the invention is defined by the appended claims rather than by the description preceding them, and all changes that fall within the metes and bounds of the claims or that form their functional as well as conjointly cooperative equivalents, are therefore intended to be embraced by these claims.

What is claimed is:

1. The method for reducing the post-restoration pain of galvanic shock from the emission of electric current in the salty saliva that normally exists in teeth on which dissimilar metal dental restorations involving formulations of amalgams, cementations, composites, composite restorations/sealants, or crown and bridge preparations have been newly placed in different areas in the patient's mouth, or next to each other in the same arch, comprising the subsequent application of a formulation, agent, or compound other than in an formulation, the essential ingredient of which is potassium nitrate comprising between 4% and 8% by weight of said formulation, agent, or compound, to the restored tooth and the cemento-enamel junction thereof after use of an formulation, until the aforesaid post-restoration dental pain is substantially reduced or entirely eliminated, said formulation being in the form of a viscous liquid gel, ointment, paste, or cream.

* * * * *